(12) United States Patent
Bouquerand et al.

(10) Patent No.: US 11,260,001 B2
(45) Date of Patent: Mar. 1, 2022

(54) PROCESS FOR PREPARING A POWDERED COMPOSITION

(71) Applicant: FIRMENICH SA, Satigny (CH)

(72) Inventors: Pierre-Etienne Bouquerand, Satigny (CH); Pascal Beaussoubre, Satigny (CH); Wolfgang Fieber, Satigny (CH); François Meyer, Satigny (CH)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 16/648,524

(22) PCT Filed: Dec. 13, 2018

(86) PCT No.: PCT/EP2018/084675
§ 371 (c)(1),
(2) Date: Mar. 18, 2020

(87) PCT Pub. No.: WO2019/115667
PCT Pub. Date: Jun. 20, 2019

(65) Prior Publication Data
US 2020/0297592 A1    Sep. 24, 2020

(30) Foreign Application Priority Data
Dec. 14, 2017  (EP) .................................... 17207503

(51) Int. Cl.
| | |
|---|---|
| *A61K 8/11* | (2006.01) |
| *A23L 27/00* | (2016.01) |
| *A23P 10/35* | (2016.01) |
| *A23P 10/40* | (2016.01) |
| *A61K 8/06* | (2006.01) |
| *A61Q 13/00* | (2006.01) |
| *A61Q 15/00* | (2006.01) |

(52) U.S. Cl.
CPC ............... *A61K 8/11* (2013.01); *A23L 27/72* (2016.08); *A23L 27/80* (2016.08); *A23P 10/35* (2016.08); *A23P 10/40* (2016.08); *A61K 8/062* (2013.01); *A61Q 13/00* (2013.01); *A61Q 15/00* (2013.01); *A23V 2002/00* (2013.01); *A61K 2800/412* (2013.01); *A61K 2800/56* (2013.01)

(58) Field of Classification Search
CPC .... A61K 8/11; A61K 8/062; A61K 2800/412; A61K 2800/56; A61K 8/046; A61K 8/25; A61K 8/732; A61K 8/0225; A61K 8/0229; A23L 27/80; A23L 27/72; A23P 10/35; A23P 10/40; A61Q 13/00; A61Q 15/00; A23V 2002/00; C11D 3/505; C11D 17/06; C11D 3/00; C11D 3/0068; C11D 3/50; C11D 11/02
See application file for complete search history.

(56) References Cited

U.S. PATENT DOCUMENTS

| | | | |
|---|---|---|---|
| 2006/0008426 A1* | 1/2006 | Doring | A61K 8/49 424/59 |
| 2007/0078071 A1* | 4/2007 | Lee | A61K 8/11 510/130 |
| 2009/0253612 A1 | 10/2009 | Mushock et al. | |
| 2010/0240608 A1* | 9/2010 | Hedges | A23L 29/20 514/61 |
| 2011/0268919 A1* | 11/2011 | Sandmeyer | C09D 7/65 428/143 |
| 2015/0190774 A1* | 7/2015 | Phipps | A23L 27/72 427/213.34 |
| 2016/0317993 A1* | 11/2016 | Rotello | A61K 8/11 |
| 2016/0354749 A1* | 12/2016 | Wu | B01J 13/16 |
| 2017/0105908 A1* | 4/2017 | Rochette | A61K 8/042 |
| 2018/0085291 A1* | 3/2018 | Sasaki | D06M 15/6436 |

FOREIGN PATENT DOCUMENTS

| | | |
|---|---|---|
| EP | 2300146 B2 | 3/2017 |
| EP | 2579976 B2 | 8/2017 |
| WO | 2007004166 A1 | 1/2007 |
| WO | 2007054853 A1 | 5/2007 |
| WO | 2007135583 A2 | 11/2007 |
| WO | 2007/137441 | * 12/2007 |
| WO | 2013092375 A1 | 6/2013 |
| WO | 2013174921 A1 | 11/2013 |
| WO | 2014044840 A1 | 3/2014 |
| WO | 2015110568 A1 | 7/2015 |
| WO | 2017134179 A1 | 8/2017 |

OTHER PUBLICATIONS

International Search Report and Written Opinion for corresponding International Application No. PCT/EP2018/084675, dated Feb. 12, 2019, 4 pages.
Written Opinion Of the International Searching Authority for corresponding International Application No. PCT/EP2018/084675, dated Feb. 12, 2019, 8 pages.

* cited by examiner

*Primary Examiner* — Gollamudi S Kishore
(74) *Attorney, Agent, or Firm* — Armstrong Teasdale LLP

(57) ABSTRACT

The present disclosure relates to the field of delivery systems. More particularly, the present disclosure relates to a process for preparing a powdered composition including granules. The granules include at least one active substance present in an encapsulated form and in a non-encapsulated form. They are obtained by drying a mixture including an aqueous phase of a water-soluble polymer, a Pickering emulsion including a non-encapsulated active substance and a microcapsule slurry including an encapsulated active substance that can differ or being the same as the non-encapsulated substance. The disclosure further relates to granules obtained by the process and to products containing them.

20 Claims, 1 Drawing Sheet

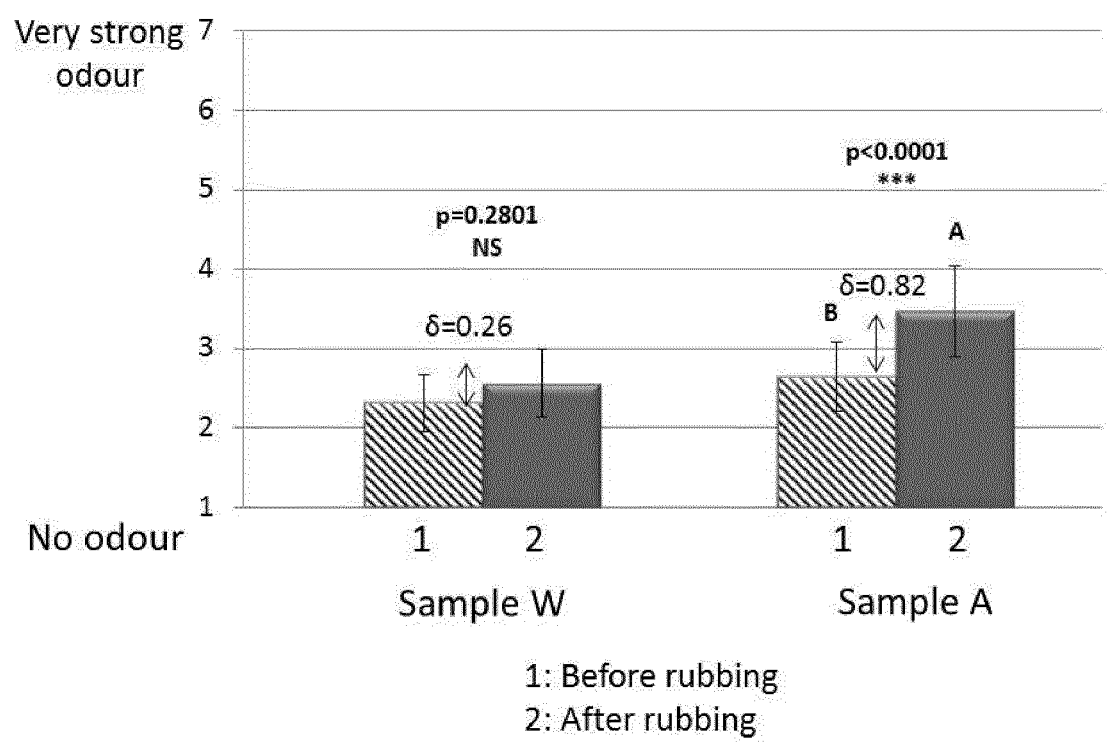

PROCESS FOR PREPARING A POWDERED COMPOSITION

This application is a U.S. National Phase Application of PCT/EP2018/084675, filed Dec. 13, 2018, which claims priority to EP Application No. 17207503.8, filed on Dec. 14, 2017, the contents of which are hereby incorporated by reference in their entirety.

TECHNICAL FIELD

The present invention relates to the field of delivery systems. More particularly, the present invention relates to a process for preparing a powdered composition comprising granules. Said granules comprise at least one active substance present in an encapsulated form and in a non-encapsulated form. These granules are obtained by drying a mixture comprising an aqueous phase of a water-soluble polymer, a Pickering emulsion comprising a non-encapsulated active substance, and a microcapsule slurry comprising an encapsulated active substance that can differ or be the same as the non-encapsulated substance. The invention further relates to granules obtained by said process and to products containing them.

TECHNICAL BACKGROUND

Fragrances and flavors play an important role in the perception of consumer product performance and thus they often determine the consumer's choice for a given product. One main advantage of encapsulated fragrance/flavor is that blooming or long-lasting of fragrance/flavor is enhanced during and after application, (e.g. after rinsing and drying of the skin or the fabrics for fragrance).

Among different techniques, spray-drying is a well-known technique for the encapsulation of flavors and fragrances. Spray-dried granules are commonly prepared from an emulsion that is sprayed into a drying chamber. The emulsion typically comprises an active substance such as a flavor or a fragrance, a carrier and an emulsifier.

Most of the time, biopolymers with surface active properties, such as for example gum Arabic, modified starches, modified cellulose, gelatin, alginates or even proteins such as albumin or beta-globulin, are used as emulsifiers.

For example, US 2009/0253612 describes a spray-dry encapsulation process for flavor or fragrance comprising drying an aqueous emulsion containing the oil to be encapsulated, modified starch and phosphate salts.

In addition, the increasing consumer demand for an intense and strong perfume or flavor release is driving the development of new delivery systems.

Indeed, depending on the applications, a dual type of triggered release can be desired: a triggered release by moisture or wetting, and a triggered release by applying mechanical action such as rubbing or shearing. The non-encapsulated fragrance or flavor oil which is entrapped in the solid polymer matrix can be spontaneously released by bringing the powdered composition into contact with water. The encapsulated fragrance or flavor oil within core-shell microcapsules can be released by mechanical action. In addition, this triggered release can be followed by a long-term release after deposition of the microcapsules onto the fabric in case of detergent applications.

The present invention is proposing a solution to the above-mentioned problem, based on a powdered composition obtained by drying a mixture comprising an aqueous phase of a water-soluble polymer, a Pickering emulsion comprising a non-encapsulated active substance, and a microcapsule slurry comprising an encapsulated active substance that can differ or being the same as the non-encapsulated substance.

DRAWINGS

FIG. 1 represents the performance of a powdered composition according to the invention in a powder detergent.

SUMMARY OF THE INVENTION

A first object of the invention is a process for preparing a powdered composition, said process comprising the steps of:
a) adding a solution of a water-soluble polymer to a Pickering emulsion, wherein the Pickering emulsion comprises
   (i) a non-encapsulated oil phase comprising a hydrophobic active ingredient, preferably a perfume or a flavour;
   (ii) solid particles that are insoluble in water; and
   (iii) water;
b) adding a core-shell microcapsule slurry to the emulsion of step a), said slurry comprising microcapsules having a polymeric shell and a core comprising encapsulated oil; and
c) drying the emulsion of step b) to obtain a powdered composition.

A second object of the invention is a powdered composition comprising granules made of:
   a water soluble polymer matrix,
   an oil phase comprising a hydrophobic active ingredient, preferably a perfume or a flavor, said oil phase being dispersed in the matrix, wherein one part of the oil phase is freely dispersed within the matrix and wherein one part of the oil phase is encapsulated in core-shell microcapsules, and
   solid particles that are insoluble in water;
   said powder being obtained by a process comprising the steps of:
a) adding a solution of a water-soluble polymer to a Pickering emulsion, wherein the Pickering emulsion comprises
   (i) a non-encapsulated oil phase comprising a hydrophobic active ingredient, preferably a perfume or a flavour;
   (ii) solid particles that are insoluble in water; and
   (iii) water;
b) adding a core-shell microcapsule slurry to the emulsion of step a), said slurry comprising microcapsules having a polymeric shell and a core comprising encapsulated oil; and
c) drying the emulsion of step b) to obtain a powdered composition.

A third object of the invention is a powdered composition comprising granules made of:
   a water soluble polymer matrix,
   an oil phase comprising a hydrophobic active ingredient, preferably a perfume or a flavor, said oil phase being dispersed in the matrix, wherein one part of the oil phase is freely dispersed within the matrix and wherein one part of the oil phase is encapsulated in core-shell microcapsules, and
   solid particles that are insoluble in water.

In a further aspect the invention relates to a consumer product comprising the granules of the invention.

DETAILED DESCRIPTION OF THE INVENTION

Unless stated otherwise, percentages (%) are meant to designate percent by weight of a composition.

When referring to "particles", "granules" or "powdered composition", percentages (%) are given for the dried composition.

According to the invention, "encapsulated oil" refers to oil that is encapsulated in a core-shell microcapsule.

By "core-shell microcapsule", or the similar, in the present invention it is meant that capsules have a particle size distribution in the micron range (e.g. a mean diameter (d(v, 0.5)) comprised between about 1 and 3000 microns, preferably between about 1 and 500 microns and more preferably between about 1 and 3000 microns and comprise an external polymeric shell and an internal continuous oil phase enclosed by the external shell. Coacervates are also part of the present invention.

By contrast, according to the invention, "non-encapsulated oil" refers to oil that is simply entrapped (or dispersed) within the polymer matrix but that is not encapsulated in a microcapsule.

Non-encapsulated oil comprises a first hydrophobic active ingredient and the encapsulated oil comprises a second hydrophobic active ingredient that can be the same or can differ from the first hydrophobic active ingredient.

Solid particles defined in the present invention are dispersible in water and serve as stabilizers, which accumulate at the interface between two immiscible liquids (typically denoted as oil and water phase) and stabilize droplets against coalescence during the Pickering emulsion formation.

The most notable difference between a Pickering emulsion and a classical emulsion is that the former one bears solid particles at the interface between two liquid phases serving as the stabilizing agent, whereas the latter uses molecular emulsifier to stabilize emulsions.

According to the invention, it should be understood that core-shell microcapsules do not correspond to solid particles as defined in the present invention. In other words, core-shell microcapsules are different from the solid particles as defined in the present invention.

The present inventors have surprisingly discovered that the release of the active ingredient from the granules of the invention is particularly advantageous, since an instantaneous fragrance release burst can be obtained from the non-encapsulated oil upon contact with water, as well as an instantaneous fragrance release burst can be obtained from the encapsulated oil by mechanical action.

Powdered Composition

A first object of the invention is a process for preparing a powdered composition, said process comprising the steps of:
a) adding a solution of a water-soluble polymer to a Pickering emulsion, wherein the Pickering emulsion comprises
    (i) a non-encapsulated oil phase comprising a hydrophobic active ingredient, preferably a perfume or a flavour;
    (ii) solid particles that are insoluble in water; and
    (iii) water;
b) adding a core-shell microcapsule slurry to the emulsion of step a), said slurry comprising microcapsules having a polymeric shell and a core comprising encapsulated oil; and
c) drying the emulsion of step b) to obtain a powdered composition.

The first step of the process defined above consists of adding a solution of a water-soluble polymer to a Pickering emulsion comprising
   a non-encapsulated oil phase comprising a hydrophobic active ingredient;
   solid particles that are insoluble in water; and
   an aqueous phase.

Hydrophobic Active Ingredient

By "hydrophobic active ingredient", it is meant any active ingredient—single ingredient or a mixture of ingredients—which forms a two-phase dispersion when mixed with water.

In a preferred aspect of the invention, the hydrophobic active ingredient is defined by a log P above 1, more preferably above 2.

Preferably, the hydrophobic active ingredient comprises at least 90% by weight, relative to the total weight of the hydrophobic active ingredient, of compounds having a log P of at least 1, more preferably it comprises at least 90% by weight of ingredients having a log P of at least 2. Even more preferably, the hydrophobic active ingredient comprises at least 99% by weight, relative to the total weight of the hydrophobic active ingredient, of ingredients having a log P of at least 1, most preferably it comprises at least 99% by weight of ingredients having a log P of at least 2. For the purpose of the present invention log P is defined as the calculated log P as obtained by calculation using the EPI suite v3.10, 2000, U.S. Environmental Protection Agency.

In a preferred aspect of the invention, the hydrophobic active ingredient is selected from flavors and fragrances. For the purpose of the present invention, the terms "flavor or fragrance" encompass flavor or fragrance ingredients or compositions of current use in the flavor and/or fragrance industry, of both natural and synthetic origin. It includes single compounds and mixtures. Specific examples of such flavor or fragrance ingredients may be found in the current literature, e.g. in Fenaroli's Handbook of flavor ingredients, 1975, CRC Press; Synthetic Food adjuncts, 1947 by M. B. Jacobs, edited by Van Nostrand; or Perfume and Flavor Chemicals by S. Arctander, 1969, Montclair, N.J. (USA). Many other examples of current flavoring and/or perfuming ingredients may be found in the patent and general literature available. The flavoring or perfuming ingredients may be present in the form of a mixture with solvents, adjuvants, additives and/or other components, generally those of current use in the flavors and fragrance industry.

"Flavoring ingredients" are well known to a person skilled in the art of aromatizing as being capable of imparting a flavor or taste to a consumer product, or of modifying the taste and/or flavor of said consumer product, or yet its texture or mouthfeel.

By "perfuming ingredients" it is understood here compounds which are used as active ingredients in perfuming preparations or compositions in order to impart a hedonic effect when applied to a surface. In other words, such compounds, to be considered as being perfuming ones, must be recognized by a person skilled in the art of perfumery as being able to impart or modify in a positive or pleasant way the odor of a composition or of an article or surface, and not just as having an odor. Moreover, this definition is also meant to include compounds that do not necessarily have an odor but are capable of modulating the odor of a perfuming composition, perfumed article or surface and, as a result, of modifying the perception by a user of the odor of such a composition, article or surface. It also contains malodor counteracting ingredients and compositions. By the term "malodor counteracting ingredient" we mean here compounds which are capable of reducing the perception of malodor, i.e. of an odor that is unpleasant or offensive to the human nose by counteracting and/or masking malodors. In a particular embodiment, these compounds have the ability to react with key compounds causing known malodors. The reactions result in reduction of the malodor materials' airborne levels and consequent reduction in the perception of the malodor.

Accordingly, in an embodiment, the hydrophobic active ingredient comprises at least 5 wt. %, preferably at least 10.%, preferably at least 20%, more preferably at least 30% and most preferably at least 40% of chemical compounds having a vapor pressure of at least 0.007 Pa at 25° C., preferably at least 0.1 Pa at 25° C., more preferably at least 1 Pa at 25° C. and most preferably at least 10 Pa at 25° C., all percentages being defined by weight relative to the total weight of the hydrophobic active ingredient. Compounds meeting these criteria are generally regarded as having a volatile character and therefore have an odor or flavor. The method of the present invention therefore allows efficient encapsulation of high amounts of volatile ingredients. According to a particular embodiment, the hydrophobic active is a mixture of a perfume oil and a neutral carrier oil selected from cosmetically acceptable solvents or emollients such as silicon oils, mineral oils, alkanes, paraffin, triglycerides, fatty acids or gums, or mixture thereof. Examples of such products, but not limited to, are Neobee, Ester gum, Damar gum, isopropyl myristate or paraffins such as Gemseal.

According to a particular embodiment, the hydrophobic active is a mixture of a flavour oil and a neutral carrier oil selected from triglycerides, fatty acids or gums, or mixture thereof. Examples of such products, but not limited to, are Neobee, Ester gum, or Damar gum.

For the purpose of the present invention the vapor pressure is determined by calculation. Accordingly, the method disclosed in "EPI suite"; 2000 U.S. Environmental Protection Agency, is used to determine the value of the vapor pressure of a specific compound or component of the hydrophobic active ingredient.

The amount of the hydrophobic active ingredient in the Pickering emulsion is preferably comprised between 5 and 67% by weight, more preferably between 10 and 50% by weight, relative to the total weight of the emulsion.

According to an embodiment, the non-encapsulated hydrophobic active ingredient and the encapsulated hydrophobic active ingredient are identical.

According to an embodiment, the non-encapsulated hydrophobic active ingredient and the encapsulated hydrophobic active ingredient are different.

Water Soluble Polymer

A "water soluble biopolymer" is intended for the purpose of the present invention as encompassing any biopolymer which forms a one-phase solution in water. Preferably, it forms a one phase solution when dissolved in water at concentrations as high as 20% by weight, more preferably even as high as 50% by weight. Most preferably it forms a one phase solution when dissolved in water at any concentration.

According to a particular embodiment, a water soluble biopolymer with a molecular weight below 100 KDa and devoid of emulsifying properties is used.

As "biopolymer devoid of emulsifying properties", it is intended for the purpose of the present invention polymers that are not surface active and are devoid of emulsifying properties with the oil phase. Suitable biopolymers devoid of emulsifying properties are soluble in water and are devoid of hydrophobic groups. Examples of biopolymers that are considered as having emulsifying properties and that are preferably excluded comprise pectin, gum Arabic, gelatin, modified starch such as octenylsuccinate starch E1450 (Capsul™, Hicap™, Puritygum™, Emcap™ etc.), modified cellulose such as ethylcellulose, hydroxypropylcellulose or hydroxypropylmethylcellulose. According to an embodiment, no molecular emulsifier is added at any stage of the process.

According to the invention, pectin, gum Arabic, gelatine, modified starch such as octenylsuccinate starch E1450 (Capsul™, Hicap™, Puritygum™, Emcap™ etc.), modified cellulose such as ethylcellulose, hydroxypropylcellulose or hydroxypropylmethylcellulose are considered as molecular emulsifiers.

According to a particular embodiment, no gum Arabic is added at any stage of the process.

According to a particular embodiment, no gelatin is added at any stage of the process.

According to a particular embodiment, no modified starch is added at any stage of the process.

According to a particular embodiment, no modified cellulose is added at any stage of the process.

Preferred water soluble biopolymers are biopolymers like polysaccharides, oligosaccharides and disaccharides. Preferred polysaccharides are starch hydrolysates with a dextrose equivalent above 2 and most preferred ones are selected from dextrins, maltodextrins, inulin, corn-syrup, and mixtures thereof. The most preferred biopolymer for use in the present invention is maltodextrin, preferable with a DE comprised between 1 and 19.

According to a particular embodiment, the water soluble biopolymer comprises, preferably consists of maltodextrin.

According to another embodiment, the water soluble biopolymer comprises maltodextrin and sucrose.

It is also particularly advantageous to use water soluble biopolymers which do not comprise any chemical substitution, meaning that the water soluble biopolymer has not been chemically (i.e. artificially) modified.

The water soluble biopolymer is added in an amount between 5 to 75% by weight, more preferably between 10 and 55% by weight, relative to the total weight of the mixture obtained in step a).

Solid Particles

The solid particles used in the emulsion are defined as any solid particle that is water-dispersible. It means that they can form a dispersion in water but they are insoluble in water (pH>6). A particle is considered as insoluble in water if its solubility is lower than 0.1% by weight.

Solid particles as defined in the present invention are not core-shell microcapsules made of an oil-based core and a polymeric shell encapsulated said core.

In one embodiment, particles have an average diameter of at most 10 μm.

In another embodiment, particles have an average diameter of at most 9 μm.

In another embodiment, particles have an average diameter of at most 8 μm.

In another embodiment, particles have an average diameter of at most 7 μm.

In another embodiment, particles have an average diameter of at most 6 μm.

In another embodiment, particles have an average diameter of at most 5 μm.

In another embodiment, particles have an average diameter of at most 4 μm.

In another embodiment, particles have an average diameter of at most 3 μm.

In another embodiment, particles have an average diameter of at most 2 μm.

In another embodiment, particles have an average diameter of at most 1 μm.

Preferred particles are those having an average diameter of at most 1 μm, more preferably of at most 500 nm.

Preferred solid particle types include the following:
- silicon oxides, such as silica (e.g. colloidal silica such as that sold under the tradename Klebosol® by AZ Electronic Materials) or silicates (e.g. synthetic silicate such as that sold under the tradename Laponite® by Rockwood Additives);
- metal oxides, hydroxides, salts of inorganic or organic acids and their mixtures (e.g. $TiO_2$, $FeO$, $Fe(OH)_2$, $FeCO_3$, $ZnO$; $MgO$, $Mg(OH)_2$, $MgCO_3$, $Mg_3(PO_4)_2$; $CaCO_3$, $CaSO_4$, $Ca_5(PO_4)_3(OH)$, $Ca_3(C_6H_5O_7)_2$);
- silver nanoparticles;
- magnesium and aluminium silicates (clays);
- latexes;
- dietary fibers such as microcrystalline cellulose, lignin and chitin;
- cells (e.g. yeast cells) or fragments thereof;
- humic acid;
- enteric polymers (such as for example Eudragit® FS 30 D and Eudragit® L 100-55 from Evonik); and
- crystals of fats or fatty acids.

Mixtures of such particle types can also be used. More preferably, the solid particle is selected from
- silicon oxides, such as silica (e.g. colloidal silica such as that sold under the tradename Klebosol® by AZ Electronic Materials) or silicates (e.g. synthetic silicate such as that sold under the tradename Laponite® by Rockwood Additives);
- metal oxides, hydroxides, salts of inorganic or organic acids and their mixtures (e.g. $TiO_2$, $FeO$, $Fe(OH)_2$, $FeCO_3$, $ZnO$; $MgO$, $Mg(OH)_2$, $MgCO_3$, $Mg_3(PO4)_2$; $CaCO_3$, $CaSO_4$, $Ca_5(PO4)_3(OH)$, $Ca_3(C_6H_5O_7)_2$);
- silver nanoparticles;
- cells (e.g. yeast cells) or fragments thereof; and
- dietary fibers such as microcrystalline cellulose, dextrins, lignin and chitin.

Most preferably, the solid particle is chosen in the group consisting of silicon oxides, silicates or metal oxides.

According to a particular embodiment, the solid particles are negatively charged.

In a preferred aspect of the invention, the active ingredient is, as defined by a log P above 1, more preferably above 2, and the solid particle is water-soluble, i.e. it disperses easily in water to form a homogeneous suspension of particles. Preferably, in the emulsion, the particle will form with the oil and the water a contact angle $θ≤90°$, more preferably $10°≤θ≤90°$. The contact angle θ is the three-phase contact angle, measured through the aqueous phase, that is made by an interface of water and oil on the particle's surface. Practically, when the contact angle is comprised within the above range the particle succeeds in stabilizing an oil in water emulsion. It is well-known in the field of colloids that the contact angle is a quantification of the wettability of the particles at an interface oil/water. A more detailed definition of the contact angle can be found in Dickinson, E., *Use of nanoparticles and microparticles in the formation and stabilization of food emulsions*, Trends in Food Science & Technology (2011).

The relative ratio of solid particles, relative to the non-encapsulated active substance is preferably comprised between 1:1 and 1:30. In another preferred embodiment, the solid particles are present in an amount of from 0.1 to 30%, preferably from 0.5 to 30% more preferably from 1 to 16% by weight, relative to the total weight of the emulsion.

In a preferred aspect of the invention, the amount of water in the Pickering emulsion is comprised between 20 and 80% by weight, relative to the total weight of the Pickering emulsion.

Optional Acid

The powdered composition can comprise an acid preferably chosen in the group consisting of ascorbic acid, citric acid, lactic acid, tannic acid, tartaric acid, malic acid, hydrochloric acid and mixtures thereof.

According to an embodiment, the acid is added in step a) when preparing the emulsion.

According to another embodiment, once the powdered composition is formed, the acid is blended with the powder.

The amount of acid is preferably comprised between 0.001:1 to 0.5:1, more preferably from 0.001:1 to 0.05:1, even more preferably from 0.005:1 to 0.05:1, relative to the amount of solid particles.

The emulsion can be formed using any known emulsifying method, such as high shear mixing, sonication or high pressure homogenization. Such emulsifying methods are well known to the person skilled in the art.

According to a particular embodiment, no molecular emulsifier is added at any step of the process.

The emulsion may also contain optional ingredients. It may in particular further contain an effective amount of a fireproofing or explosion suppression agent. The type and concentration of such agents in spray-drying emulsions is known to the person skilled in the art. One can cite as non-limiting examples of such fireproofing or explosion suppression agents inorganic salts, $C_1$-$C_{12}$ carboxylic acids, salts of $C_1$-$C_{12}$ carboxylic acids and mixtures thereof. Preferred explosion suppression agents are, salicylic acid, acetic acid, propionic acid, butyric acid, isobutyric acid, valeric acid, caproic acid, citric acid, succinic acid, hydroxysuccinic acid, maleic acid, fumaric acid, oxylic acid, glyoxylic acid, adipic acid, lactic acid, tartaric acid, ascorbic acid, the potassium, calcium and/or sodium salts of any of the aforementioned acids, and mixtures of any of these. Other optional ingredients include antioxidants, preservatives, colorants and dyes.

Step b) of the process defined above consists of adding a core-shell microcapsule slurry to the emulsion of step a).

Preferably, the amount of oil in microcapsules added in step b) represents from ½₀ to ½, more preferably from ⅒ to ⅓ relative to the oil phase (encapsulated and not encapsulated).

The nature of the polymeric shell of the microcapsules of the invention can vary. As non-limiting examples, the shell can be made of a material selected from the group consisting of polyurea, polyurethane, polyamide, polyacrylate, polysiloxane, polycarbonate, polysulfonamide, urea formaldehyde, melamine formaldehyde resin, melamine formaldehyde resin cross-linked with polyisocyanate or aromatic polyols, melamine urea resin, melamine glyoxal resin, gelatin/gum arabic shell wall, and mixtures thereof.

According to a particular embodiment, the shell of the microcapsule is a hydrogel shell. Examples of processes for the preparation of coacervates are for instance described in WO2013/174921, WO2014/044840, contents of which is also included by reference.

According to an embodiment, the shell of the microcapsule is based on melamine formaldehyde resin or melamine formaldehyde resin cross-linked with at least one polyisocyanate or aromatic polyols.

According to another embodiment, the shell of the microcapsule is polyurea-based.

The shell can also be a hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to an embodiment, the shell comprises an aminoplast copolymer, such as melamine-formaldehyde or urea-formaldehyde or cross-linked melamine formaldehyde or melamine glyoxal.

According to a particular embodiment, the core-shell microcapsules are cross-linked melamine formaldehyde microcapsules obtainable by a process comprising the steps of:
1) admixing a perfume oil with at least a polyisocyanate having at least two isocyanate functional groups to form an oil phase;
2) dispersing or dissolving into water an aminoplast resin and optionally a stabilizer to form a water phase;
3) adding the oil phase to the water phase to form an oil-in-water dispersion, wherein the mean droplet size is comprised between 1 and 100 microns, by admixing the oil phase and the water phase;
4) performing a curing step to form the wall of said microcapsule; and
5) optionally drying the final dispersion to obtain a dried core-shell microcapsule;

This process is described in more details in WO 2013/092375 and WO 2015/110568, the contents of which are included by reference.

According to another embodiment the shell is polyurea-based made from, for example but not limited to isocyanate-based monomers and amine-containing crosslinkers such as guanidine carbonate and/or guanazole. Preferred polyurea-based microcapsules comprise a polyurea wall which is the reaction product of the polymerization between at least one polyisocyanate comprising at least two isocyanate functional groups and at least one reactant selected from the group consisting of an amine (for example a water soluble guanidine salt and guanidine); a colloidal stabilizer or emulsifier; and an encapsulated perfume. However, the use of an amine can be omitted.

According to another embodiment, the shell is polyurethane-based made from, for example but not limited to polyisocyanate and polyols, polyamide, polyester, etc.

According to a particular embodiment the colloidal stabilizer includes an aqueous solution of between 0.1% and 0.4% of polyvinyl alcohol, between 0.6% and 1% of a cationic copolymer of vinylpyrrolidone and of a quaternized vinylimidazole (all percentages being defined by weight relative to the total weight of the colloidal stabilizer). According to another embodiment, the emulsifier is an anionic or amphiphilic biopolymer preferably chosen from the group consisting of polyacrylate (and copolymers especially with acrylamide), gum arabic, soy protein, gelatin, sodium caseinate and mixtures thereof.

According to a particular embodiment, the polyisocyanate is an aromatic polyisocyanate, preferably comprising a phenyl, a toluyl, a xylyl, a naphthyl or a diphenyl moiety. Preferred aromatic polyisocyanates are biurets and polyisocyanurates, more preferably a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N).

According to a particular embodiment, the polyisocyanate is a trimethylol propane-adduct of xylylene diisocyanate (commercially available from Mitsui Chemicals under the tradename Takenate® D-110N).

The preparation of an aqueous dispersion/slurry of core-shell microcapsules is well known from a skilled person in the art. In one aspect, said microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Mo. U.S.A.), Cytec Industries (West Paterson, N.J. U.S.A.), Sigma-Aldrich (St. Louis, Mo. U.S.A.).

According to a particular embodiment, the core-shell microcapsule is a formaldehyde-free capsule. A typical process for the preparation of aminoplast formaldehyde-free microcapsules slurry comprises the steps of:
1) preparing an oligomeric composition comprising the reaction product of, or obtainable by reacting together
   a) a polyamine component in the form of melamine or of a mixture of melamine and at least one $C_1$-$C_4$ compound comprising two $NH_2$ functional groups;
   b) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
   c) a protic acid catalyst;
2) preparing an oil-in-water dispersion, wherein the droplet size is comprised between 1 and 600 um, and comprising:
   i. an oil;
   ii. a water medium
   iii. at least an oligomeric composition as obtained in step 1;
   iv. at least a cross-linker selected amongst
   A) $C_4$-$C_{12}$ aromatic or aliphatic di- or tri-isocyanates and their biurets, triurets, trimmers, trimethylol propane-adduct and mixtures thereof; and/or
   B) a di- or tri-oxiran compounds of formula
   A-(oxiran-2-ylmethyl)$_n$
      wherein n stands for 2 or 3 and 1 represents a $C_2$-$C_6$ group optionally comprising from 2 to 6 nitrogen and/or oxygen atoms;
   v. optionally a $C_1$-$C_4$ compounds comprising two $NH_2$ functional groups;
3) heating said dispersion;
4) cooling said dispersion.

This process is described in more details in WO 2013/068255, the content of which is included by reference.

According to another embodiment, the shell of the microcapsule is polyurea- or polyurethane-based. Examples of processes for the preparation of polyurea- and polyureathane-based microcapsule slurry are for instance described in WO2007/004166, EP 2300146, EP2579976 the contents of which is also included by reference. Typically a process for the preparation of polyurea- or polyurethane-based microcapsule slurry include the following steps:
- a) dissolving at least one polyisocyanate having at least two isocyanate groups in an oil to form an oil phase;
- b) preparing an aqueous solution of an emulsifier or colloidal stabilizer to form a water phase;
- c) adding the oil phase to the water phase to form an oil-in-water dispersion, wherein the mean droplet size is comprised between 1 and 500 µm, preferably between 5 and 50 µm;
- d) applying conditions sufficient to induce interfacial polymerization and form microcapsules in form of a slurry.

According to the invention, it should be understood that, after encapsulation, whatever the nature of the microcapsule(s), the internal core of the capsule is only made of the core oil composed of a perfume oil.

The granules defined in the present invention can contain microcapsules which can vary by the core perfume oil inside them and/or by the wall (different chemistries or same chemistries but different process parameters like cross-linking temperature or duration).

According to a particular embodiment of the invention, the microcapsules have an outer coating selected from the group consisting of a non-ionic polysaccharide, a cationic polymer and mixtures thereof.

Such coating will help drive capsule deposition and retention on substrate during the wash process so that a significant part of the capsules which have not been broken in the wash phase/upon lathering would transfer to the substrate (skin, hair fabrics) and be available for perfume release when the capsules are broken upon rubbing after drying.

Non-ionic polysaccharide polymers are well known to a person skilled in the art. Preferred non-ionic polysaccharides are selected from the group consisting of locust bean gum, xyloglucan, guar gum, hydroxypropyl guar, hydroxypropyl cellulose and hydroxypropyl methyl cellulose.

Cationic polymers are also well known to a person skilled in the art. Preferred cationic polymers have cationic charge densities of at least 0.5 meq/g, more preferably at least about 1.5 meq/g, but also preferably less than about 7 meq/g, more preferably less than about 6.2 meq/g. The cationic charge density of the cationic polymers may be determined by the Kjeldahl method as described in the US Pharmacopoeia under chemical tests for Nitrogen determination. The preferred cationic polymers are chosen from those that contain units comprising primary, secondary, tertiary and/or quaternary amine groups that can either form part of the main polymer chain or can be borne by a side substituent directly connected thereto. The weight average (Mw) molecular weight of the cationic polymer is preferably between 10,000 and 2M Dalton, more preferably between 50,000 and 3.5M Dalton.

According to a particular embodiment, one will use cationic polymers based on acrylamide, methacrylamide, N-vinylpyrrolidone, quaternized N,N-dimethylaminomethacrylate, diallyldimethylammonium chloride, quaternized vinylimidazole (3-methyl-1-vinyl-1H-imidazol-3-ium chloride), vinylpyrrolidone, acrylamidopropyltrimonium chloride, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride. Preferably copolymers shall be selected from the group consisting of polyquaternium-5, polyquaternium-6, polyquaternium-7, polyquaternium10, polyquaternium-11, polyquaternium-16, polyquaternium-22, polyquaternium-28, polyquaternium-43, polyquaternium-44, polyquaternium-46, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride As specific examples of commercially available products, one may cite Salcare® SC60 (cationic copolymer of acrylamidopropyltrimonium chloride and acrylamide, origin: BASF) or Luviquat®, such as the PQ 11N, FC 550 or Style (polyquaternium-11 to 68 or quaternized copolymers of vinylpyrrolidone origin: BASF), or also the Jaguar® (C13S or C17, origin Rhodia).

Step c) of the process defined above consists of drying the mixture obtained in step b) to obtain powdered composition.

There is no limitation regarding the way to obtain the dried particles.

Among those methods, one may cite for example the spray-drying that is a well-known method for the encapsulation of active ingredient.

However, one may cite also other drying method such as the extrusion, the fluidized bed, or even a drying at room temperature using materials (carrier, desiccant) that meet specific criteria (see for example WO2017134179).

According to a particular embodiment, step c) consists of spray-drying the mixture of step b).

The emulsion is first subjected to a spraying step during which the emulsion is dispersed in the form of drops into a spraying tower. Any device capable of dispersing the emulsion in the form of drops can be used to carry out such dispersion. For instance, the emulsion can be guided through a spraying nozzle or through a centrifugal wheel disk. Vibrated orifices may also be used.

In one aspect of the invention the emulsion is dispersed in the form of drops into a cloud of powdering agent present in the dry tower. Such type of process is for example described in details in WO2007/054853 or in WO2007/135583.

For a specific formulation, the size of the granules is influenced by the size of the drops that are dispersed into the tower. When a spraying nozzle is used for dispersing the drops, the size of such drops can be controlled by the flow rate of an atomizing gas through the nozzle, for example. In the case where a centrifugal wheel disk is used for dispersal, the main factor for adjusting droplet size is the centrifugal force with which the drops are dispersed from the disk into the tower. The centrifugal force, in turn, depends on the speed of rotation and the diameter of the disk. The feed flow rate of the emulsion, its surface tension and its viscosity are also parameters controlling the final drop size and size distribution. By adjusting these parameters, the skilled person can control the size of the drops of the emulsion to be dispersed in the tower.

Once sprayed in the chamber, the droplets are dried using any technique known in the art. These methods are perfectly documented in the patent and non-patent literature in the art of spray-drying. For example, Spray-Drying Handbook, $3^{rd}$ ed., K. Masters; John Wiley (1979), describes a wide variety of spray-drying methods.

The process of the present invention may be performed in any conventional spraying tower. A conventional multi-stage drying apparatus is for example appropriate for conducting the steps of this process. It may comprise a spraying tower, and, at the bottom of the tower, a fluidized bed intercepting partially dried granules after falling through the tower.

The amount of flavour or fragrance lost during the spray drying step is preferably below 25%, more preferably below 20%, most preferably below 10%, these percentages being defined by weight, relative to the theoretical amount that would be present in the granules if there was absolutely no flavour or fragrance lost during the spray-drying step. Another object of the invention is a powdered composition comprising granules made of:
- a water soluble polymer matrix,
- an oil phase comprising a hydrophobic active ingredient, preferably a perfume or a flavor, said oil phase being dispersed in the matrix, wherein one part of the oil phase is freely dispersed within the matrix and wherein one part of the oil phase is encapsulated in core-shell microcapsules, and
- solid particles that are insoluble in water.
- All embodiments described previously are as defined above for the powdered composition.
- According to the invention, it should be understood that solid particles are inside the granules at the interface between the non-encapsulated oil phase and the water soluble polymer matrix.

In a preferred aspect of the invention the size of the granules is typically of at least 10 µm, preferably at least 20 µm. Depending on the process used for spray-drying, in particular when a powdering agent is present in the drying tower, as described above, the dry granules can have an average size of up to 300 or even up to 750 µm. In a preferred embodiment of the invention, the average size of the granules is at least 5 times larger than the average size of the oil droplets in the emulsion.

According to an embodiment, the oil phase comprises at least one part that is encapsulated, preferably in an amount comprised between 0.25 and 30%, preferably between 0.5 and 20%, based on the total weight of the powdered composition.

The amount of active substance in the powdered composition is preferably comprised between 5 and 67% by weight, more preferably between 10 and 50% by weight, relative to the total weight of the powdered composition.

According to a particular embodiment, the powdered composition consists of granules.

Another object of the invention is a powdered composition comprising granules made of:
- a water soluble polymer matrix,
- an oil phase comprising a hydrophobic active ingredient, preferably a perfume or a flavor, said oil phase being dispersed in the matrix, wherein one part of the oil phase is freely dispersed within the matrix and wherein one part of the oil phase is encapsulated in core-shell microcapsules, and
- solid particles that are insoluble in water;
- said powder being obtained by a process comprising the steps of:
  a) adding a solution of a water-soluble polymer to a Pickering emulsion, wherein the Pickering emulsion comprises
    (i) a non-encapsulated oil phase comprising a hydrophobic active ingredient, preferably a perfume or a flavour;
    (ii) solid particles that are insoluble in water; and
    (iii) water;
  b) adding a core-shell microcapsule slurry to the emulsion of step a), said slurry comprising microcapsules having a polymeric shell and a core comprising encapsulated oil; and
  c) drying the emulsion of step b) to obtain a powdered composition.
All embodiments described above for the process also apply for the powdered composition.

Consumer Product

In another aspect, the invention relates to a consumer product comprising the granules of the invention. Preferably such product is a flavored or fragranced product.

Preferably, the flavored product is a food product. The consumer product of the invention preferably is a particulate or powdery flavored or fragranced product. In such a case, the granules of the invention may easily be added thereto by dry-mixing.

In a preferred aspect of the invention, the food product is selected from the group consisting of an instant soup or sauce, a breakfast cereal, a powdered milk, a baby food, a powdered drink, a powdered chocolate drink, a spread, a powdered cereal drink, a chewing gum, an effervescent tablet, a cereal bar, and a chocolate bar. The powdered foods or drinks may be intended to be consumed after reconstitution of the product with water, milk and/or a juice, or another aqueous liquid.

According to a particular embodiment, the flavored product is a food product and granules of the invention comprise coacervates core-shell microcapsules.

In an embodiment the fragranced product is a powdery product. Preferably it is a powder or a tablet detergent, a make-up, a deodorant or an antiperspirant, in particular aerosol antiperspirants and stick antiperspirants.

According to a particular embodiment, the consumer product is a tablet detergent composition and comprises detergent active ingredients and the powder composition as defined above.

Detergent active ingredients include those well-known in the art for use in powder laundry detergents such as, surfactants (anionic, nonionic, cationic or zwititterionic) in particular surfactant particles made by spray-drying, bleaching agents like percarbonate and bleach activator (such as Tetraacetylethylenediamine—TAED), buffering agent like sodium carbonate, sodium bicarbonate, sodium silicate; builder like phosphate, zeolite, sodium carbonate, polyacrylate (co)polymers; soil release or soil suspension polymers; granulated enzyme particles; antifoaming or sud suppressor agents; dye, silicone or clay softening agents or filler like sodium sulphate.

According to another embodiment, the consumer is in the form of an antiperspirant or deodorant active composition and comprises:
- an antiperspirant or deodorant active ingredient, and
- the powdered composition as defined above.

As used herein, the term "antiperspirant or deodorant product" refers to the normal meaning in the art; i.e. a composition applied on skin allowing to reduce or prevent body odour.

Exemplary products include wax-based sticks, soap-based sticks, compressed powder sticks, roll-on suspensions or solutions, emulsions, gels, creams, squeeze sprays, pump sprays, aerosols, and the like. Each product form may contain its own selection of additional components, some essential and some optional. The types of components typical for each of the above product forms may be incorporated in the corresponding compositions presented herein.

Antiperspirant or deodorant active ingredients are preferably incorporated in an amount of from 0.5-50%, particularly from 5 to 30% of the weight of the composition.

Antiperspirant or deodorant active ingredients may include astringent metallic salts, especially inorganic and organic salts of aluminum, zirconium and zinc, as well as mixtures thereof. Even more specifically, antiperspirant actives or deodorant active ingredients may be selected from the group consisting of aluminum chloride, aluminum chlorohydrate, aluminum chlorohydrex, aluminum chlorohydrex PG, aluminum chlorohydrex PEG, aluminum dichlorohydrate, aluminum dichlorohydrex PG, aluminum dichlorohydrex PEG, aluminum sesquichlorohydrate, aluminum sesquichlorohydrex PG, aluminum sesquichlorohydrex PEG, aluminum sulfate, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY and aluminum zirconium trichlorohydrate GLY.

Granules defined in the present invention are preferably incorporated in an amount of from 0.4% to 10%, particularly from 0.4% to 5%, more preferably from 0.4% to 2% of the weight of the composition.

Free perfume can be added in an amount comprised between 0.1 and 8%, preferably between 0.1 and 4% by weight based on the total weight of the composition.

Depending of the type of product, the deodorant or antiperspirant product may comprise supplementary ingredients enabling to obtain the desired form. Non-limiting examples of suitable ingredients include emollient(s), solubilizer(s), antioxidant(s), preservative(s), carrier(s), odour entrapper(s), propellant(s), primary structurant(s), additional chassis ingredient(s), volatile silicone solvent(s), gellant(s), buffering agent and residue masking material(s). A person skilled in the art is able to select them on the basis of its general knowledge and according to intended form of the deodorant or antiperspirant composition.

For example, by way of illustration, a roll-on deodorant or antiperspirant product may comprise water, emollient, solubilizer, antioxidants, preservatives, or combinations thereof; a clear gel product or antiperspirant product may comprise water, emollient, solubilizer, malodour-absorbing material, antioxidants, preservatives, ethanol, or combinations thereof; a body spray may contain a carrier, odour entrappers, propellant, or combinations thereof; an invisible solid deodorant or antiperspirant product may contain a primary structurant, and additional chassis ingredient(s); a soft solid deodorant or antiperspirant product may comprise volatile silicone, gellant, residue masking material, or combinations thereof; an aerosol deodorant or antiperspirant product may comprise a carrier, a propellant, or a combination thereof.

Emollients suitable for deodorant or antiperspirant products include, but are not limited to, propylene glycol, polypropylene glycol (like dipropylene glycol, tripropylene glycol, etc.), diethylene glycol, triethylene glycol, neopentyl glycol diheptanoate, PEG-4, PEG-8, 1,2-pentanediol, 1,2-hexanediol, hexylene glycol, glycerin, $C_2$ to $C_{20}$ monohydric alcohols, $C_2$ to $C_{40}$ dihydric or polyhydric alcohols, alkyl ethers of polyhydric and monohydric alcohols, dicaprylyl carbonate, dicaprylyl ether, diethylhexylcyclohexane, dibutyl adipate, volatile silicone emollients such as cyclopentasiloxane, nonvolatile silicone emollients such as dimethicone, mineral oils, polydecenes, petrolatum, and combinations thereof. One example of a suitable emollient comprises PPG-15 stearyl ether. Other examples of suitable emollients include dipropylene glycol and propylene glycol.

The composition of the invention can include any topical material that is known or otherwise effective in preventing or eliminating malodour, including malodour associated with sweat and/or perspiration. Suitable material may be selected from the group consisting of antimicrobial agents (e.g., bacteriocides, fungicides), malodour-absorbing material, and combinations thereof.

Antimicrobial agents may comprise cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof.

A suitable solubilizer can be, for example, a surfactant, such as a no-foaming or low-foaming surfactant. Suitable surfactants are nonionic surfactants, cationic surfactants, amphoteric surfactants, zwitterionic surfactants, and mixtures thereof. Suitable solubilizers include, for example, polyethylene glycol ether of Cetearyl Alcohol, hydrogenated castor oil such as polyoxyethylene hydrogenated castor oil, polyoxyethylene 2 stearyl ether, polyoxyethylene 20 stearyl ether, and combinations thereof.

Suitable preservatives include organic sulfur compounds, halogenated compounds, cyclic organic nitrogen compounds, low molecular weight aldehydes, parabens, propane diol materials, isothiazolinones, quaternary compounds, benzoates, low molecular weight alcohols, dehydroacetic acid, phenyl and phenoxy compounds, or mixtures thereof.

Non-limiting examples of commercially available preservatives include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathan® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name German® II from Sutton Laboratories, Inc.; N,N"-methylenebis {N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, German 115® from Sutton Laboratories, Inc.; polymethoxy bicyclic oxazolidine, available under the trade name Nuosept® C from Hills America; formaldehyde; glutaraldehyde; polyaminopropyl biguanide, available under the trade name Cosmocil CQ® from ICI Americas, Inc., or under the trade name Mikrokill® from Brooks, Inc.; dehydroacetic acid; and benzsiothiazolinone available under the trade name Koralone™ B-119 from Rohm and Hass Corporation.

Suitable levels of preservative can range from about 0.0001% to about 0.5%, alternatively from about 0.0002% to about 0.2%, alternatively from about 0.0003% to about 0.1%, by weight of the composition.

Suitable carriers can include, water, alcohol, or combinations thereof. Useful alcohols include $C_1$-$C_3$ alcohols. In some aspects, the alcohol is ethanol.

Some examples of propellants include compressed air, nitrogen, inert gases, carbon dioxide, and mixtures thereof. Propellants may also include gaseous hydrocarbons like propane, n-butane, isobutene, cyclopropane, and mixtures thereof; e.g. A-46 (a mixture of isobutane, butane and propane), A-31 (isobutane), A-17 (n-butane), A-108 (propane), AP70 (a mixture of propane, isobutane and nbutane), AP40 (a mixture of propane, isobutene and n-butane), AP30 (a mixture of propane, isobutane and n-butane). Some non-limiting examples of propellants include 1,1-difluoroethane, 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof.

The term "primary structurant" as used herein means any material known or otherwise effective in providing suspending, gelling, viscosifying, solidifying, and/or thickening properties to the composition or which otherwise provide structure to the final product form. These primary structurants include gelling agents, and polymeric or non-polymeric or inorganic thickening or viscosifying agents. Such materials will typically be solids under ambient conditions and include organic solids, crystalline or other gellants, inorganic particulates such as clays or silicas, or combinations thereof. Non-limiting examples of suitable primary structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fischer-Tropsch waxes, and microcrystalline wax; polyethylenes with molecular weight of 200 to 1000 daltons; solid triglycerides; behenyl alcohol, or combinations thereof.

Chassis ingredients may be an additional structurant such as stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fisher-Tropsch waxes, and microcrystalline wax; polyethylenes with molecular weight of 200 to 1000 daltons; and solid triglycerides; behenyl alcohol, or combinations thereof; non-volatile organic fluids such as mineral oil, PPG-14 butyl ether, isopropyl myristate, petrolatum, butyl stearate, cetyl octanoate, butyl myristate, myristyl myristate, C12-15 alkylbenzoate (e.g., Finsolv™), octyldodecanol, isostearyl isostearate, octododecyl benzoate, isostearyl lactate, isostearyl palmitate or isobutyl stearate; clay mineral powders such as talc, mica, sericite, silica, magnesium silicate, synthetic fluorphlogopite, calcium silicate, aluminum silicate, bentonite and montomorillonite; pearl pigments such as alumina, barium sulfate, calcium secondary phosphate, calcium carbonate, titanium oxide, finely divided titanium oxide, zirconium oxide, zinc oxide, hydroxy apatite, iron oxide, iron titrate, ultramarine blue, Prussian blue, chromium oxide, chromium hydroxide, cobalt oxide, cobalt titanate, titanium oxide coated mica; organic powders such as polyester, polyethylene, polystyrene, methyl methacrylate resin, cellulose, 12-nylon, 6-nylon, styrene-acrylic acid copolymers, poly propylene, vinyl chloride polymer, tetrafluoroethylene polymer, boron nitride, fish scale guanine, laked tar color dyes, laked natural color dyes; and combinations thereof.

Volatile silicone solvents suitable for use in the antiperspirant compositions include, but are not limited to, solvent such as Cyclomethicone D-5; GE 7207 and GE 7158 (commercially available from General Electric Co.); Dow Corning 344; Dow Corning 345; Dow Corning 200; and DC1184 (commercially available from Dow Corning Corp.); and SWS-03314 (commercially available from SWS Silicones).

The gellant material may comprise saturated or unsaturated, substituted or unsubstituted, fatty alcohols or mixtures of fatty alcohols having from about 20 to about 60 carbons atoms, alternatively from about 20 to about 40 carbon atoms. In some embodiments, the gallant materials comprise combinations of the fatty alcohols. In some embodiments, the fatty alcohol gellants are may be saturated, unsubstituted monohydric alcohols or combinations thereof, which have a melting point of at less than about 110° C., alternatively from about 60° to about 110° C., alternatively between about 100° C. and 110° C.

Specific examples of fatty alcohol gellants for use in the antiperspirant products that are commercially available include, but are not limited to, Unilin® 425, Unilin® 350, Unilin® 550 and Unilin® 700 (supplied by Petrolite).

A suitable buffering agent may be alkaline, acidic or neutral. The buffer may be used in the composition or product for maintaining the desired pH. Suitable buffering agents include, for example, hydrochloric acid, sodium hydroxide, potassium hydroxide, and combinations thereof.

Non-limiting examples of suitable residue masking materials for use in the antiperspirant products include butyl stearate, diisopropyl adipate, petrolatum, nonvolatile silicones, octyldodecanol, phenyl trimethicone, isopropyl myristate, $C_{12-15}$ ethanol benzoates and PPG-14 Butyl Ether.

The deodorant or antiperspirant products disclosed herein may comprise other optional ingredients such as emulsifiers, distributing agents, antimicrobials, pharmaceutical or other topical actives, surfactants, and the like.

The nature, amount and type of ingredients does not warrant a more detailed description here, which in any case would not be exhaustive, the skilled person being able to select them on the basis of its general knowledge and according to intended form.

In some aspects, the deodorant or antiperspirant composition comprises less than 95 wt % of water, relative to the total weight of the composition. In some aspects, the composition comprises less than 90 wt % of water, relative to the total weight of the composition. In some aspects, the composition comprises less than 85 wt % of water, relative to the total weight of the composition. In some aspects, the composition comprises less than 80 wt % of water, relative to the total weight of the composition. In some aspects, the composition comprises less than 75 wt % of water, relative to the total weight of the composition. In some aspects, the composition comprises less than 70 wt % of water, relative to the total weight of the composition. In some aspects, the composition comprises less than 65 wt % of water, relative to the total weight of the composition. In some aspects, the composition comprises less than 60 wt % of water, relative to the total weight of the composition. In some aspects, the composition comprises less than 55 wt % of water, relative to the total weight of the composition. In some aspects, the composition comprises less than 50 wt %, or less than 40 wt %, or less than 30 wt %, or less than 20 wt %, or less than 10 wt % of water, relative to the total weight of the deodorant or antiperspirant composition. In some aspects, the composition is water-free.

EXAMPLES

The invention will now be described in further detail by way of the following examples.

Example 1

Preparation of Powdered Composition According to the Invention

1. Synthesis of Microcapsules Containing a Perfume Oil (Microcapsules 1)

TABLE 1

Composition of slurry of core-shell microcapsules 1

| Ingredient | [%] |
|---|---|
| Oil Phase | |
| Perfume oil [a] | 34.59 |
| Water phase | |
| Water | 48.27 |
| Melamine/formaldehyde copolymer[1] | 2.67 |
| Melamine/formaldehyde copolymer[2] | 0.30 |
| Acrylamide/acrylic acid copolymer[3] | 5.60 |
| Acetic acid | 0.21 |
| Ethylene urea 50% solution | 7.28 |
| Xanthan gum | 0.43 |
| Preservative agent[4] | 0.16 |
| NaOH 30% solution | 0.49 |
| Total | 100 |

[1] Urecoll ®SMV (origin: BASF)
[2] Cymel ®9370 (origin: Allnex)
[3] Alcapsol (origin: BASF)
[4] Kathon ™CG (origin: Dow Chemical)

TABLE 2

Composition of perfume A

| Component | % |
|---|---|
| ALLYL HEPTANOATE | 39.0 |
| UNDECALACTONE GAMMA | 23.0 |
| ISOPROPYL MYRISTATE | 11.0 |
| BETA IONONE | 20.5 |
| HEXYL SALICYLATE | 6.5 |

2. Preparation of the Powdered Composition According to the Invention (Sample A)

300 g of Perfume B (see table 3) were added to a dispersion of 30 g of silica particles (Aerosil® 380F) and 1.50 g of citric acid in 668 g of distilled water. The resulting mixture was homogenized with one pass in a high pressure homogenizer (Lab2000-APV Alberslund—Denmark). The first stage was set at a pressure of 320 bars while the second stage was set at a pressure of 90 bars. 100 g of the resulting "Pickering" emulsion was then dispersed, using a simple propeller head stirrer (mild agitation), into 170 g of a solution composed by 70 g of 18 DE Maltodextrin (Origin: Roquette) and 100 g of deionized water. Then 10 g of a slurry of microcapsules 1 were added using the same mixing device to form the spray-feed. The spray-feed was dried using a laboratory spray-drier (Mini Büchi B-290 Flawil—Switzerland) with an inlet temperature set at 180° C. and the throughput was adapted to get an outlet temperature of 90° C. producing a dry powder (Sample A). The total perfume content in the spray-dried granules was measured by low-field NMR using the proper calibration. The yield in atomization was estimated by comparing the measured total amount of perfume with the theoretical content that would be achieved without any losses during the spray-drying process.

TABLE 3

Composition of perfume B

| Component | % |
|---|---|
| ACÉTATE DE 4-(1,1-DIMÉTHYLÉTHYL)-1-CYCLOHEXYLE [1] | 14.5 |
| LINALOL BJ | 10.5 |
| LILIAL ®[2] | 10.0 |
| ISO E SUPER [3] | 10.0 |
| CITRONELLYL NITRILE | 9.0 |
| DIPHENYLOXYDE | 6.5 |
| ISOBORNYL ACETATE | 6.0 |
| BETA IONONE | 6.0 |
| TRICYCLO[5.2.1,0~2,6~]DEC-3-EN-8-YL ACETATE (A) + TRICYCLO[5.2.1,0~2,6~]DEC-4-EN-8-YL ACETATE (B)[4] | 5.5 |
| ETHER MT | 4.0 |
| HEDIONE ® [5] | 4.0 |
| GERANIOL 60 | 3.0 |
| CITRAL | 2.5 |
| ALDEHYDE C 10 | 2.5 |
| ALLYL HEPTANOATE | 2.5 |
| ETHYL METHYL-2-BUTYRATE | 1.5 |
| GERANYL ACETATE | 1.0 |
| 2,4-DIMETHYL-3-CYCLOHEXENE-1-CARBALDEHYDE [6] | 1.0 |

[1] Firmenich SA, Switzerland
[2] 3-(4-tert-butylphenyl)-2-methylpropanal, Givaudan SA, Vernier, Switzerland
[3] 1-(octahydro-2,3,8,8-tetramethyl-2-naphtalenyl)-1-ethanone, International Flavors & Fragrances, USA
[4] Firmenich SA, Switzerland
[5] Methyl dihydrojasmonate, Firmenich SA, Switzerland
[6] Firmenich SA, Switzerland

TABLE 4

Composition of powdered composition (sample A)

| Components | % |
|---|---|
| Perfume B | 25.94 |
| Hydrophilic silica | 2.59 |
| Citric acid | 0.13 |
| Maltodextrin | 60.54 |
| Microcapsules | 10.80 |
| Total perfume | 33 |
| Perfume content by LF-NMR | 25.90 |
| Encapsulation yield | 78.50 |

Microcapsules comprise oil and encapsulating material. Yield analysis showed that only 21.50% of perfume was lost during spray-drying.

Example 2

Preparation of Comparative Powdered Composition According to the Invention (Sample Z)

10 g of slurry of microcapsules 1 were added to a clear solution composed of 29.2 g of maltodextrin 18 DE (Roquette France) and 48.3 g of deionized water. Then 30 g of perfume B were added to the previous mixture under constant agitation using laboratory static mixer (Ultra Turrax®IKA). This spray-feed was kept under agitation using magnetic stirrer and dried using a laboratory spray-drier (Mini Büchi B-290 Flawil—Switzerland) with an inlet temperature set at 180° C. and the throughput was adapted to get an outlet temperature of 90° C. producing a dry powder (Sample Z). The total perfume content in the spray-dried granules was measured by low-field NMR using the proper calibration. The yield in atomization was estimated by comparing the measured total amount of perfume with the theoretical content that would be achieved without any losses during the spray-drying process.

TABLE 5

| Composition of powdered composition (sample Z) | |
| --- | --- |
| Components | % |
| Perfume B | 26.65 |
| Hydrophilic silica | 0.00 |
| Citric acid | 0.00 |
| Maltodextrin 18 DE | 62.26 |
| Microcapsule slurry I | 11.09 |
| | 100.00 |
| Perfume content by LF-NMR | 12.30% |
| Encapsulation yield | 36.20% |

Microcapsules comprise oil and encapsulating material. Yield analysis showed that about 63.80% of perfume was lost during spray-drying.

Compared to sample A, the result show that particles are essential in the emulsion to stabilize oil droplets and enhance the yield in hydrophobic active upon drying.

Example 3

Preparation of Comparative Powdered Composition According to the Invention (Sample W)

In a 200 ml beaker, 3 g of silica was weighed. The suspension was completed to 66.85 g with water. 30 g of perfume B was then added to the suspension, and the solution was emulsified for 2 min. using an ultrasonic probe (sonotrode H14 tip 14) connected on a Hielscher UP400S ultrasonic processor. Average droplet size was checked to be around 2 microns using microscopy. Emulsion 1 is obtained (see table 6 below).

TABLE 6

| Composition of emulsion | |
| --- | --- |
| Compound | Emulsion 1 (%) |
| Silica [1] | 3 |
| Perfume B [2] | 30 |
| Citric acid | 1.5 |
| Water | 66.85 |
| TOTAL | 100 |

[1] Aerosil ® 380 (origin: Evonik)
[2] See table 3

To 100 g of the previous emulsion, 70 g of a Maltodextrin18DE (50% solution) was added to get the spray feed solution 1 (see table 7 below).

TABLE 7

| Composition of spray feed solution 1 | |
| --- | --- |
| Compound | Spray feed solution 1 (%) |
| Silica [1] | 1.25 |
| Perfume B [2] | 12.5 |
| Citric acid | 0.06 |
| Maltodextrin [3] | 29.17 |
| Water | 57.02 |
| TOTAL | 100 |

[1] Aerosil ® 380 (origin: Evonik)
[2] See table 3
[3] Glucidex ®18DE (origin: Roquette)

Spray-drying was performed using a Büchi B-290. Entrance temperature was measured at 180° C., while the temperature at the exit was between 86° C. and 97° C.

The final powder granules were composed exclusively of silica particles, Maltodextrin 18DE, citric acid and were loaded with about 29.08% of perfume oil (see table 8).

TABLE 8

| Composition of the powdered composition 1 | |
| --- | --- |
| Compound | Powdered composition 1 (%) |
| Silica | 2.9 |
| Perfume B | 29.08 |
| Citric acid | 0.15 |
| Maltodextrin [3] | 67.87 |
| TOTAL | 100 |

Example 4

Antiperspirant Composition Comprising Powdered Composition of the Invention

Sample A is introduced in a AP/Deo aerosol formulation (see table 9) and in a AP/Deo Stick formulation (see table 10).

TABLE 9

| AP/Deo aerosol formulation | |
| --- | --- |
| Compound | Amount (%) |
| Cyclomethicone [1] | 53.01 |
| Isopropyl Myristate [2] | 8.96 |
| Silica [3] | 1.02 |
| Quaternium-18 Hectorite [4] | 3.33 |
| Aluminium Chlorohydrate [5] | 32.75 |
| Sample A | 0.93 |
| | 100.00 |

[1] Dow Corning 345 Fluid (origin: Dow Corning)
[2] Isopropyl Myristate (origin: Firmenich SA, Switzerland)
[3] Aerosil ®200 (origin: Evonik)
[4] Bentone ® 38 (origin: Elementis Specialties)
[5] Micro Dry Ultrafine (Origin: SummitReheis)

TABLE 10

AP/Deo Stick formulation

| Compound | Amount (%) |
| --- | --- |
| Cyclomethicone[1] | 54.01 |
| Stearyl Alcohol[2] | 20.62 |
| PPG-14 Butyl Ether[3] | 1.96 |
| Hydrogenated Castor Oil[4] | 0.98 |
| Aluminium Zirconium tetrachlorohydrex-Gly[5] | 19.64 |
| Sample A | 2.79 |
|  | 100.00 |

[1] Dow Corning 345 Fluid (origin: Dow Corning)
[2] Lanette ®18 (origin: BASF)
[3] Tegosoft ® PBE (origin: Evonik)
[4] Cutina ® HR (origin: BASF)
[5] Summit AZP-908 (aluminium zirconium tetrachlorohydration glycin; origin: SummitReheis)
6) Perfume (origin: Firmenich SA, Switzerland)

Example 5

Performance of powdered composition according to the invention in a powder detergent 2 kg of cotton laundry (20 towels and 4 ballasts) were washed in a Miele Novotronic W 900-79 Ch washing machine (40° C. short cycle without pre-wash at 900 rpm, followed by 2 rinsing cycles).

80 g powder detergent (Sodium carbonate, sodium dodecylbenzenesulfonate, sodium silicate, aqua, zeolite, C12-15 pareth 7, citric acid, sodium acrylic acid/MA copolymer, stearic acid, sodium chloride, corn starch modified, tetrasodium etidronate, cellulose gum, calcium sodium EDTMP, sodium bicarbonate, kaolin, sodium polyacrylate, peptides, subtilisin, cellulose, dextrin, calcium carbonate, PEG-75, imidiazolinone, aluminium silicate, mannamase, methione, DIPG) containing the perfumed compositions described in the examples were used (sample A @0.60% and comparative sample W @0.75%).

After the washing, the laundry was dried for 24 hours.

A sensory panel was performed with 18 Panellists that were asked to rate the perfume intensity on dry towels before and after rubbing using a scale between 1 (non-perceptible perfume) and 7 (very strong perfume intensity).

The panels' results were then analysed with a 95% confidence interval (or 90% if needed) and variance was calculated using Duncan's post-hoc analysis (alpha=0.05).

Results are displayed in FIG. 1.

Intensities after rubbing are significantly more intense than before rubbing for sample A. One can conclude from those results that there is a rubbing effect for sample A (according to the invention comprising both encapsulated oil and non-encapsulated oil) compared to sample W devoid of encapsulated oil.

Example 6

Preparation of Powdered Composition According to the Invention (Sample B)

In a 400 ml beaker, 2 g of silica was weighed. The suspension was completed to 170 g with water. 30 g of orange oil was then added to the suspension, and the solution was emulsified for 2 min. using an ultrasonic probe (sonotrode H14 tip 14) connected on a Hielscher UP400S ultrasonic processor. Average droplet size was checked to be around 3 microns using microscopy. Emulsion B is obtained (see table 11 below).

TABLE 11

Composition of emulsion B

| Compound | Concentration (%) |
| --- | --- |
| Silica [1] | 1 |
| Orange oil [2] | 15 |
| Water | 84 |
| TOTAL | 100 |

[1] Aerosil ®380 (origin: Evonik)
[2] Orange oil, origin: Firmenich SA, Switzerland To 200 g of the previous emulsion, 58 g of a Maltodextrin18DE was added, then 24.8 g of a microcapsules slurry (containing 34.65% of limonene) to get the spray feed solution (see table 12 below).

TABLE 12

Composition of spray feed solution

| Compound | Concentration (%) |
| --- | --- |
| Emulsion B | 70.7 |
| Maltodextrin [1] | 20.5 |
| Microcapsules slurry [2] | 8.8 |
| Water | 59.41 |
| TOTAL | 100 |

[1] Glucidex ®18DE (origin: Roquette)
[2] Microcapsules slurry (34.65% limonene - see protocol of example 1), origin: Firmenich S.A., Switzerland Spray-drying was performed using a Büchi B-290. Entrance temperature was measured at 180° C., while the temperature at the exit was between 86° C. and 97° C. The final powder granules were composed exclusively of silica particles, Maltodextrin 18DE, polymeric microcapsules, and were loaded with about 21.7% of oil measured using LF-NMR (Oxford instruments, UK) Hahn-Spin-Echo analysis based on a calibration performed on 18 DE maltodextrin and limonene.

Example 7

Preparation of Comparative Powdered Composition (Sample Y)

In a 200 ml beaker 30 g of maltodextrin 18 DE and 30 g Capsul™ emulsifying modified starch of were dissolved in 70 g of water under agitation until forming an homogenous solution. Then 30 g of orange oil were dispersed into the solution using a rotor/stator mixer (IKA T25 Ultra Turrax) to form a homogeneous emulsion. Then 24.8 g of microcapsules slurry (containing 34.65% limonene) is incorporated into the emulsion using a propeller head mixer. The resulting liquid is the spray-feed solution ready to be processed.

TABLE 13

Composition of the spray-feed solution.

| Compound | Concentration (%) |
| --- | --- |
| Maltodextrin [1] | 16.2 |
| Modified starch [2] | 16.2 |

TABLE 13-continued

| Composition of the spray-feed solution. | |
|---|---|
| Compound | Concentration (%) |
| Orange oil [3] | 16.2 |
| Microcapsules slurry [4] | 13.4 |
| Water | 37.9 |
| TOTAL | 100 |

[1] Glucidex ®18DE origin: Roquette
[2] Capsul ®, origin Ingredion
[3] Orange oil, origin: Firmenich SA, Switzerland
[4] Microcapsules slurry (34.65% limonene- see protocol example 1), origin: Firmenich S.A., Switzerland Spray-drying was performed using a Büchi B-290. Entrance temperature was measured at 180° C., while the temperature at the exit was between 86° C. and 97° C. The final powder granules were composed exclusively of modified starch, Maltodextrin 18DE, polymeric microcapsules and were loaded with about 21.9% of oil measured by Low-Field NMR using LF-NMR (Oxford instruments, UK) Hahn-Spin-Echo analysis based on a calibration performed on 18 DE maltodextrin and limonene.

Example 8

Release Performance

The release of volatile limonene from the dry powder of sample B and sample Y before dissolution in water was monitored with a portable photoionization detector (Model Tiger, IonScience).

Between 50 mg and 100 mg of the spray-dried powder was mixed with maltodextrine MD 18 DE in a ratio of 1:3. The total quantity of oil was equal in all experiments. The samples were placed into the headspace cell, the cell was closed and the detector was connected to the air outlet. The headspace concentration was measured continuously at intervals of 1 second. The measured headspace concentration reached a plateau after 5 to 10 minutes.

TABLE 14

| volatile concentration in the gas phase above the solid powders after five minutes. | |
|---|---|
| Sample B gas concentration [ppm] | Sample Y gas concentration [ppm] |
| 21.1 | 62.2 |

The spray dried emulsion according to the invention sample B shows systematically lower gas phase concentrations than the comparative sample Y above the solid powder, showing therefore a more efficient retention of the volatile oil in the solid matrix.

Example 9

Release Performance Upon Dissolution in Water

The release of volatile limonene after dissolution of sample B and sample Y in water was monitored with a portable photoionization detector (Model Tiger, IonScience).

Between 50 mg and 100 mg of the spray-dried powder was mixed with maltodextrine MD 18 DE in a ratio of 1:3 in order to ensure a proper, complete and instantaneous dispersion of the powder once in contact with water. The total quantity of oil was equal in all experiments. The samples were placed into the headspace cell, the cell was closed and the detector was connected to the air outlet. The headspace concentration was measured continuously at intervals of 1 second. After equilibration of 5 minutes 10 mL of water or buffer solution was added through a septum and simultaneously stirring was started. The headspace was measured for another 5 minutes.

After an initial burst phase of volatile release that typically lasts for about 60 seconds the signal quickly drops to a plateau value, followed by an exponential decay until complete evaporation of the volatile. The maximum volatile concentration in the gas phase after dilution was determined for each sample.

TABLE 15

| volatile concentration in the gas phase after dilution | | | |
|---|---|---|---|
| Dissolution medium | pH | Sample B gas concentration [ppm] | Sample Y gas concentration [ppm] |
| 100 mM citrate buffer | 3.5 | 502.8 | 274.7 |
| 100 mM phosphate buffer | 7.0 | 544.1 | 367.0 |

The spray dried emulsion according to the invention sample B shows systematically higher gas phase concentrations than the comparative sample Y, showing therefore a more efficient release of the volatile oil upon dissolution of the powder in aqueous applications.

The invention claimed is:

1. A process for preparing a powdered composition, said process comprising the steps of:
    a) adding a solution of a water-soluble polymer to a Pickering emulsion, wherein the Pickering emulsion comprises
       (i) a non-encapsulated oil phase comprising a hydrophobic active ingredient;
       (ii) solid particles that are insoluble in water; and
       (iii) water;
    b) adding a core-shell microcapsule slurry to the emulsion of step a), said slurry comprising microcapsules having a polymeric shell and a core comprising an encapsulated oil phase; and
    c) drying the emulsion of step b) to obtain a powdered composition;
    wherein the powdered composition comprises the encapsulated oil phase and the non-encapsulated oil phase upon drying,
    wherein no molecular emulsifier is added at any stage of the process.

2. The process according to claim 1, wherein step c) consists of spray-drying the mixture.

3. The process according to claim 1, wherein a hydrophobic active ingredient comprises at least 90% by weight, relative to the total weight of the hydrophobic active ingredient, of compounds having a log P of at least 1.

4. The process according to claim 1, wherein the polymeric shell of the core-shell microcapsule slurry is made of a material selected from the group consisting of polyurea, polyurethane, polyamide, polyacrylate, polysiloxane, polycarbonate, polysulfonamide, urea formaldehyde, melamine formaldehyde resin, melamine formaldehyde resin cross-linked with polyisocyanate or aromatic polyols, melamine urea resin, melamine glyoxal resin, gelatin/gum arabic shell wall and mixtures thereof.

5. The process according to claim 1, wherein a weight ratio between the encapsulated oil phase and the non-encapsulated oil phase is between 1/20 and 1/2.

6. The process according to claim 1, wherein the water-soluble polymer is chosen in the group consisting of malto-dextrin, inulin, corn syrup, dextrin, and mixtures thereof.

7. The process according to claim 1, wherein the solid particles have an average diameter of at most 10 μm.

8. The process according to claim 1, wherein the solid particles are selected from the group consisting of:
    silicon oxides;
    metal oxides, hydroxides, salts of inorganic or organic acids and their mixtures;
    silver nanoparticles;
    magnesium and aluminium silicates;
    latexes;
    dietary fibers;
    cells or fragments thereof;
    humic acid;
    enteric polymers; and
    crystals of fats or fatty acids.

9. The process according to claim 1, wherein the solid particles are silicon oxides, silicates or metal oxides.

10. A powdered composition comprising granules made of:
    a water soluble polymer matrix,
    an oil phase comprising a hydrophobic active ingredient, said oil phase being dispersed in the matrix, wherein one part of the oil phase is freely dispersed within the matrix and wherein one part of the oil phase is encapsulated in core-shell microcapsules, and
    solid particles that are insoluble in water;
    said powder being obtained by a process comprising the steps of:
    a) adding a solution of a water-soluble polymer to a Pickering emulsion, wherein the Pickering emulsion comprises
        (i) a non-encapsulated oil phase comprising a hydrophobic active ingredient;
        (ii) solid particles that are insoluble in water; and
        (iii) water;
    b) adding a core-shell microcapsule slurry to the emulsion of step a), said slurry comprising microcapsules having a polymeric shell and a core comprising encapsulated oil; and
    c) drying the emulsion of step b) to obtain a powdered composition,
    wherein no molecular emulsifier is added at any stage of the process.

11. A consumer product comprising the powdered composition according to claim 10.

12. The consumer product according to claim 11, wherein said product is a flavoured or fragranced product.

13. The consumer product according to claim 11 in the form of a powder detergent or an antiperspirant or deodorant composition.

14. The process according to claim 1, wherein the hydrophobic active ingredient is a perfume or a flavour.

15. The process according to claim 5, wherein the weight ratio between the encapsulated oil phase and the non-encapsulated oil phase is between 1/10 and 1/3.

16. The powdered composition comprising according to claim 10, wherein the oil phase of the granules comprises a perfume or a flavor.

17. The powdered composition comprising according to claim 10, wherein the non-encapsulated oil phase of the Pickering emulsion comprises a perfume or a flavor.

18. The powdered composition comprising according to claim 10, wherein the oil phase of the granules comprises a perfume or a flavor and the non-encapsulated oil phase of the Pickering emulsion comprises a perfume or a flavor.

19. The process according to claim 1, wherein a total amount of the encapsulated oil phase and the non-encapsulated oil phase lost during the drying step c) is below 25% by weight.

20. The process according to claim 1, wherein a total amount of the encapsulated oil phase and the non-encapsulated oil phase present in the obtained powdered composition is from 10% to 50%, by weight of the powdered composition.

* * * * *